United States Patent [19]

Wrasidlo

[11] Patent Number: 5,731,334
[45] Date of Patent: Mar. 24, 1998

[54] METHOD FOR TREATING CANCER USING TAXOID ONIUM SALT PRODRUGS

[75] Inventor: Wolfgang Wrasidlo, Heuberer Torwag, Germany

[73] Assignee: The Scripps Research Institute, La Jolla, Calif.

[21] Appl. No.: 549,282

[22] Filed: Oct. 27, 1995

Related U.S. Application Data

[63] Continuation-in-part of PCT/US95/00478, Jan. 10, 1995, PCT/US95/00481, Jan. 10, 1995, PCT/US95/00538, Jan. 10, 1995, said PCT/US95/00478 is a continuation-in-part of Ser. No. 180,034, Jan. 11, 1994, abandoned, said PCT/US95/00481 is a continuation-in-part of Ser. No. 549,282, Oct. 27, 1995, abandoned, said PCT/US95/00538 is a continuation-in-part of 180,136, Jan. 11, 1994, abandoned.

[51] Int. Cl.$^6$ ............. A61K 31/44; A61K 31/335; C07D 405/12; C07D 305/14
[52] U.S. Cl. ............. 514/358; 514/449; 546/281.7; 549/510; 549/511
[58] Field of Search ............. 549/510, 517; 514/449, 358; 546/281.7

[56] References Cited

U.S. PATENT DOCUMENTS

| | | | |
|---|---|---|---|
| 4,942,184 | 7/1990 | Haugwitz et al. | 514/449 |
| 4,960,790 | 10/1990 | Stella et al. | 514/449 |
| 5,422,364 | 6/1995 | Nicolaou et al. | 514/449 |

FOREIGN PATENT DOCUMENTS

0473326A1  8/1991  European Pat. Off. .

OTHER PUBLICATIONS

Swindell et al., J. Med. Chem. '91, 34, 1176–1184.
Zhao et al., J. of Natural Prod. 1991, 54, 1607–1611.
Mathew et al., J. Med. Chem. 1992, 35, 145–151.
Nicolaou et al. Nature, 1993, 364, 464–466.
Longnecker et al., Cancer Treat. Rep., 1987, 71, 53–59.
Mukaiyama, Angew. Chemie. 1979, 18, 707–808.
Nicolaou, J Chem Comm, 1993, 1024–1025.
Nicolaou et al., J. Chem. Soc., 116, 1994, 1591.
Nicolaou et al., Angew. Chem, 1994, 33, 1583.
Nicolaou et al., Angew Chem, 1994, 33, 1581–1583.
Paloma et al., Chem and Biol. 1, 1994, 107–112.
Nicolaou et al., New Perspectives in Drug Design, Acad. Press, 1995, 69.
Nicolaou et al., J.Chem Comm. 1992, 1117–1118.
Nicolaou et al., J. Chem Comm. 1992, 1118–1120.
Nicolaou et al., Nature 1994, 367, 630–634.
Nicolaou et al., J. Chem Comm. 1994, 295–296.
Nicolaou et al., J. Am. Chem. Soc. 1995, 117, 624–633.
Nicolaou et al., J. Am. Chem. Soc 1995, 117, 634–644.
Nicolaou et al., J. Am. Chem. Soc 1995, 117, 645–652.
Nicolaou et al., J. Am. Chem. Soc 1995, 117, 653–659.
Deutsh et al., J. Med. Chem, 1989, 32, 788–792.

*Primary Examiner*—Ba K. Trinh
*Attorney, Agent, or Firm*—Donald G. Lewis

[57] ABSTRACT

C-2'-methylpyridinium acetates (MPA)-taxol and C-2'-methylpyridinium acetates (MPA)-taxotere are prodrugs having good aqueous solubility, low toxicity and high anti-minor activity. These prodrugs are administered to patients for treating minors. Adminstration may be by injection or infusion.

17 Claims, 6 Drawing Sheets

1: Taxol

5: Taxotere

2: Taxol-2'-MPA; R1=Ph,R2=Ac
6: Taxotere-2'-MPA; R1=OtBu,R2=OH

3: Taxol-7-MPA; R1=Ph,R2=Ac

4: 2-(3-Thiophenoyl)-taxol-2'-MPA

7: Taxol-2'-acylsulfonylcarboxylic acid

METHOD FOR TREATING CANCER USING TAXOID ONIUM SALT PRODRUGS

CROSS-REFERENCE TO RELATED APPLICATION

The present application is a continuation-in-part of pending PCT patent application Ser. No. US95/00478, filed Jan. 10, 1995, which is a continuation-in-part of U.S. patent application Ser. No. 08/180,034, filed Jan. 11, 1994, now abandoned, the disclosures of which is incorporated herein by reference. The present application is also a continuation-in-part of pending PCT patent application Ser. No. US95/00481 filed Jan. 10, 1995, which is a continuation-in-part of U.S. patent application Ser. No. 08/180,135, filed Jan. 11, 1994, now abandoned, the disclosures of which is incorporated herein by reference. The present application is also a continuation-in-part of pending PCT patent application Ser. No. US95/00538, filed Jan. 10, 1995 which is a continuation-in-part of U.S. patent application Ser. No. 08/180,136, filed Jan. 11, 1994, now abandoned, the disclosures of which is incorporated herein by reference.

GOVERNMENT RIGHTS

The invention disclosed herein was supported in part by Grant Number CA46446-CH from the National Institutes of Health. The United States government may have certain rights to this invention.

FIELD OF INVENTION

The invention relates to a medical use of taxoid onium salt prodrugs for treating patients with tumors or other cancers.

BACKGROUND

Taxol (paclitaxel; Bristol-Myers Squibb Co, Wallingford Conn.) is a diterpene compound of novel structure which has been isolated from the bark of the Northwestern or Japanese yew tree *Taxus brevifolia* (Rowinsky et. al. *J. Natl Cancer Inst.* 1990 82, 1247). In vitro, taxol has been shown to promote the assembly of microtubules (Schiff et. al. *Nature* 1979, 227, 655) and to stabilize tubulin polymers against depolymerization (Schiff et. al. *Proc. Natl. Acad. Sci.* 1980, 77, 1561). Other antimicrotubular agents act primarily by inhibiting the microtubular system; however, taxol exerts its effect on the $G_2$ and M phases of the cell cycle by binding to tubulin, thus enhancing the rate and extent of microtubular polymerization and stabilizing formed microtubules. The result is a rigid microtubular network that resists depolymerization and inhibits cellular replication (Manfredi et. al. *Pharmacol Ther* 1984, 25, 83). In addition, taxol has been shown to activate macrophages to express TNF-a and IL-1 and to downregulate TNF-receptors; both of these activities are shared by bacterial LPS (Manthey et. al. *J. Immunology* 1992 149, 2459; Ding et. al. *Science* 1990, 248, 370). This cytokine stimulatory activity of taxol may contribute to its antitumor properties.

Taxol has recently been approved for clinical use in the treatment of refractory ovarian and breast cancers in the United States (Markman et. al. *Yale Journal of Biology and Medicine* 1991 64, 583; McGuire et. al. *Ann. Intern. Med.* 1989 111, 273). It is a potential candidate for chemotherapy of other neoplasms including breast (Holmes et. al. *J. Nat. Cancer Inst.* 1991 83, 1797), skin (Einzig et. al. *Proc. Am. Soc. Clin. Oncol* 1988, 7, 249), lung (Ettinger et. al. *Sem. Oncol.* 1993, 20, 46) and head and neck carcinomas (Forastire et. al. *Sem. Oncol.* 1990, 20, 56). The compound also shows potential for the treatment of polycystic kidney disease (Woo et. al. *Nature* 1994 368, 750).

Taxol dose intensity has been shown to be an important factor in the treatment of patients with ovarian cancer (Sarosy et. al. *J. Natl Med Assoc* 1993, 85, 427). A phase I study was undertaken by the National Cancer Institute which examined taxol dose intensification with a granulocyte colony-stimulating factor (G-CSF) support (Sarosy et. al. *J. Clinical Oncology* 1992 10, 1165). In this study, patients were treated with increasing doses of taxol to determine the maximally tolerated taxol dose when drug-related hematologic toxicity is ameliorated. The study showed that patients tolerated 250 mg/m$^2$ of taxol administered as a 24 hour intravenous infusion every 3 weeks when followed by a G-CSF dose of 10 mg/kg/day. Granulocyte colony-stimulating factor was administered daily through the granulocyte nadir. At a dose of 300 mg/m$^2$/day, the dose limiting toxicity was peripheral neuropathy. The severe neurologic toxicity was brief, resolving within several days or weeks after the onset of symptoms (Sarosy et. al. *Proc. ASCO* 1992 11, 226).

Another phase I study was performed using alternating sequences of taxol and cisplatin on untreated and minimally pretreated solid tumor patients (Rowinsky et. al. *J. of Clinical Oncology* 1991 9, 1692). Sequential dose escalation of each agent using taxol doses of 100 or 135 mg/m$^2$ and cisplatin doses of 50 or 75 mg/m$^2$ resulted in four dosage permutations that induced grades 3 and 4 neutropenia in 72% to 84% and 50% to 53% of courses studied. At the highest taxol-cisplatin dose level (200 mg/m$^2$ to 75 mg/m$^2$) the mean neutrophil count nadir was 98☐ µL and hospitalization for neutorpenia and fever was required in 64% of courses. The starting doses of taxol (110 mg/m$^2$) and cisplatin (50 mg/m$^2$) were doses that produce minimal toxicity when either drug was administered as a single agent. The doses of both agents were then escalated to within a conventional range, focusing on dose escalation of taxol. The dose levels were 135/50, 110/75, 135/75, 170/75, and 200/75 mg/m$^2$.

Taxol was supplied as a concentrated sterile solution (6 mg/mL) in a 5 mL ampule in 50% polyoxyethylated castor oil (Cremophor EL) and 50% dehydrated alcohol. Because of stability considerations 25% of the total dosage was reconstituted immediately before use in 250 mL of 5% dextrose in water and was infused over 6 hours for four treatments. Glass bottles and polyethylene-lined nitro glycerin tubing were use to administer taxol due to possible problems with Cremophor-induced leaching of plasticizers. Due to the association of HSRs with taxol's Cremophor vehicle, and fewer of these reactions being noted with prolonged infusions and medications, taxol was administered over 24 hours with the following premedications: 1) dexamethasone, 20 mg intravenously (IV) or orally, 14 and 7 hours before taxol; (2) diphenhydramine, 50 mg (IV) 30 minutes before taxol; and either one of the $H_2$-histamine antagonists, ranitidine 50 mg IV or famotidine 20 mg IV, 30 minutes before taxol. Continuous EGG telemetry was performed during the infusion of taxol. (Rowinsky et. al. *J. of Clinical Oncology* 1991 9, 1692).

A phase I study of taxol (paclitaxel) has recently been performed with pediatric patients having refractory solid tumors. (Hurwitz et. al. *Clinical Oncology* 1993 11, 2324; Sonnichsen et. al. *J. Clinical Oncology* 1994 12, 532). Thirty one children (age, 2.3 to 22.8 years) were given escalating doses of taxol (200 to 420 mg/m$^2$) as a 24 hour intravenous (IV) continuous infusion. Taxol was supplied as a concentrated sterile solution in 50% polyoxyethylated castor oil (Cremophor EL) and 50% dehydrated ethanol. Because of the risk for hypersensitivity reactions, all patients were premedicated with dexamethasone (0.25 mg/kg at −14 hours and −7 hours) and diphenhydramine (1.0 mg/kg at −30 minutes) before administration of taxol. The taxol was administered as a 24 hour continuous intravenous (IV) infusion in 5% dextrose at an initial concentration of 0.5 mg/mL. Dose escalation above the starting dose (200 mg/m$^2$) proceeded in 20% increments (240, 290, 350, and 420 mg/m$^2$) until dose-limiting toxicity was reached. The dose-limiting toxicity was neurotoxicity which occurred at a dose of 420 mg/m$^2$. It is suggested that the recommended dose of paclitaxel for continuing phase II studies, based on this pediatric population, is 350 mg/m$^2$/d. This is substantially greater than the usual adult dosages for solid tumor patients (110 to 250 mg/m$^2$). An observation from this study is that children appear to tolerate significantly larger doses of taxol than adults (Sonnichsen et. al. *J. Clinical Oncology* 1994 12, 532; Legha et. al. Cancer 1990 65, 2478).

Taxotere (N-debenzoyl-N-tert-butoxycarbonyl-10-deacetyl Taxol; RP 56976; NSC 628503, Rhone Poulenc Rorer Research Development ) is a semisynthetic analogue of taxol which is twice as active in inhibiting tubuline depolymerization and has demonstrated better in vivo activity on B 16 melanoma with responses in several advanced adenocarcinomas. In a phase I study, sixty five patients (49 women, 16 men), with a median age of 57 years, each received 248 courses of Taxotere administered as a 1–2 hour I.V. infusion every 2 or 3 weeks. Ten distinct dosage levels from 5 to 115 mg/m$^2$ were studied (Extra et. al. *Cancer Research*, 1993 53, 1037). It was found that dose-dependent, reversible neutorpenia was the limiting toxicity. Delayed and cumulative skin reactions occurred beyond 70 mg/m$^2$ and alopecia was observed in the majority of patients beyond 70 mg/m$^2$. The recommended dose from this schedule is 100 mg/m$^2$ every 3 weeks (Extra et. al. *Cancer Research*, 1993 5.3, 1037). Taxoterel has recently been approved for clinical use in the treatment of refractory breast cancers in the United States.

The taxotere used for the study was supplied by Rhone Poulenc Rorer laboratories in 15 mg/ml vials in 50% polysorbate 80 (Tween 80) and 50% dehydrated alcohol. The vials were reconstituted just prior to use in 50 cc of 5% dextrose in water and the amount of Taxotere was further diluted in 5% dextrose in water, so that the maximum Taxotere concentration was 0.3 mg/ml to ensure that polysorbate 80 concentration would not exceed 1%. No pretreatment medication to prevent gastrointestinal toxicity or anaphylactic reactions was given. Taxotere was give at intervals of 2 weeks and then at an interval of 3 weeks when side-effects were observed, which was doses greater than 55 mg/m$^2$. Treatment was stopped in cases of severe toxicity; a cohort of 3 patients was studied at each dose level until significant toxicity was observed. (Extra et. al. *Cancer Research*, 1993 53, 1037.)

A generally recognized shortcoming of taxol is its low solubility in aqueous media conventionally employed for administering drugs. The low solubility of taxol necessitates its formulation in mineral oil suspensions, e.g., Cremophor EL, in order to achieve concentrations sufficient to administer an effective dose. Unforunately, the presence of a mineral oil suspension exacerbates the undesirable side effect of taxol in patients.

Deutsch et al (*J. Med. Chem.*, 1989: vol. 32, pp 788–792) disclose a C-2' substituted amino amide derivative whose hydrochloride salt exhibits good solubility, high potency and good in vivo efficacy. However, the compound has poor stability. Zhao and Kingston (*J. Natural Products*, 1991: vol. 54, pp 1607–1611) have improved the stability of the 2' substitutes amino derviatives by preparing sufonate salts which are neutral and more stable. Unfortunately, these compounds have significantly less in vivo activity than taxol.

What are needed are taxol and taxotere prodrugs having superior antitumor activites, low toxicity, and good solubility.

SUMMARY

It is disclosed herein that the C-2' onium salts of taxol and taxotere achieve good solubility while maintaining a high level of anti-tumor activity and low toxicity in vivo. C-2' onium salts of taxol and taxotere release taxol and taxotere respectively upon exposure to plasma, thereby serving as a prodrug of the parent compound.

It is also disclosed herein that the in vivo anti-tumor activity of C-2' substituted taxoids depends upon the pharmacokinetics of prodrug reversion to the parent compound. The pharmacokinetics of the prodrug are determined by a balance between in vivo hydrolytic stability, bioavailability, and the rate of elimination.

It is also disclosed herein that hi vitro activities of taxoid onium salts are poorly correlated and unpredictive with respect to in vivo anti-tumor activities. The C-7 onium salts of taxol actively bind to tubulin and are selectively cytotoxic against transformed cells in vitro but have a poor anti-tumor efficacy in vivo. Both the C-2' and the C-7 onium salts of taxol exhibit relatively high cytotoxicity profiles with IC$_{50}$ values in vitro in the nanomolar range for tumor cell lines. However, these in vitro findings are largely uncorrelated with antiproliferation effects observed in various nude mouse models. The nature of the substituents for a given position as well as the location of a given substituent at different positions in the molecule have profound effects on the antitumor activity of the compounds. This could not be predicted from the in vitro data. The 7-substituted pyridinium salt of taxol (3) was as effective as taxol in inhibiting calcium induced microtubule disassembly and showed cytotoxicities comparable to taxol on human tumor cell lines. However, these same 7-substituted pyridinium salts completely failed to inhibit the growth of these tumors in nude mice. The 2'-substituted acyl derivative of taxol (7), which exhibits a high cytotoxicity profile and behaves as a prodrug, completely fails to exhibit any antitumor effects in vivo. On the other hand, the 2'-onium salt (2) exhibited no tubulin binding, and in competition assays of intact cells showed affinity profiles three orders of magnitude below that of the parent taxol. However, when tested in vivo, this compound produced tumor regression with a high percentage of animals being free of measurable tumor masses at the end of the experiments. Furthermore, this compound was well tolerated, showing no visible toxic side effects and no significant weight loss in tumor beating nude mice. When taxol was administered in mice on an equal molar basis, both visual toxicity and animal weight losses were observed. On the other hand, when taxol was administered at somewhat lower doses, its efficacy was significantly diminished, indicating that taxol exhibits a relatively narrow therapeutic window. The much higher plasma affinity of the onium salts may be one reason for their improved tolerance in animals.

Accordingly, one aspect of the invention is directed to a method for treating a mammal having a tumor or other cancer. The tumor is treated by administering an aqueous solution of a taxoid onium salt prodrug. The route of administration may be by injection or infusion. The taxoid onium salt prodrug is represented by the following structure:

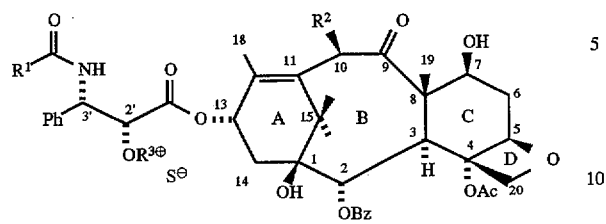

wherein S⁻ is selected from the group consisting of OAc⁻, Cl⁻, Br⁻, I⁻, BF₄⁻, ClO₄⁻, ArSO₃⁻, and AlkylSO₃⁻, $R^1$ is selected from the group consisting of phenyl and tBuO, $R^2$ is selected from the group consisting of OAc and OH, and $R^3$ is represented by the following structure:

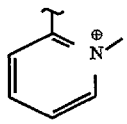

The method of the invention may be employed with any mammal, including human tumor or cancer patients. In one of the preferred modes of the invention, the mammal is sensitive and/or intolerant to a side effect of taxol. Taxol-2'-MPA is much less toxic in vivo than taxol or taxotere.

A preferred dosage for treating tumors and other cancers is approximately 50–300 mg/m². Alternatively, when treating tumors requiring a high therapeutic index, the preferred dosage is approximately 50–4,900 mg/m². When treating refractory tumors or cancers, the preferred dosage is approximately 50–21,000 mg/m² and in some cases approximately 50–28,000 mg/m². At a high dosage, the method of the invention is particularly useful for treating tumors or other cancers that are refractory and/or insensitive to taxol.

In an alternative mode, the method of the invention may employ any counter ion S⁻ that is classified as generally regarded as safe (GRAS) by the U.S. Food and Drug Administration.

Preferred routes of administration include injection of a bolus and infusion. The administration may be intravenous or intraperitoneal.

A preferred taxoid onium salt prodrug taxol-2'-MPA is represented by the following structure:

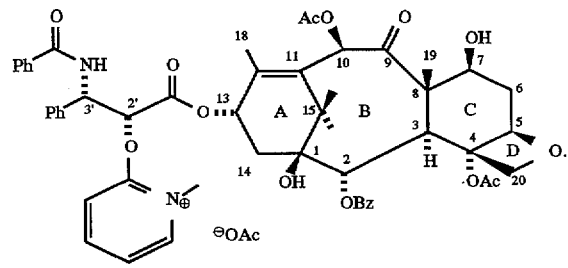

An alternative preferred prodrug onium salt is taxotere-2'-MPA represented by the following structure:

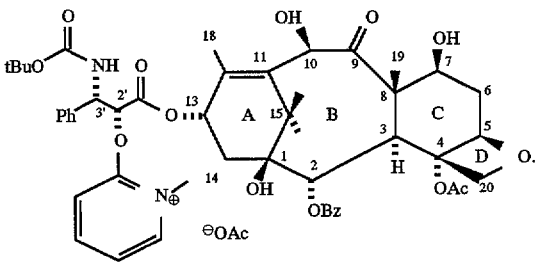

DETAILED DESCRIPTION

Human Tumor Xenografts in Nude Mice

Figure 1:
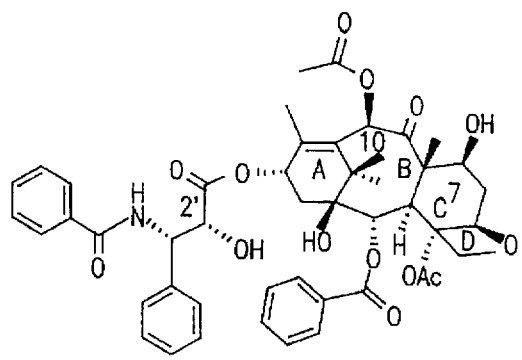
FIG. 1 illustrates the chemical structures of taxol, taxotere, and C-2', C-7, and C-2 substitutes derivatives.
Figure 1:
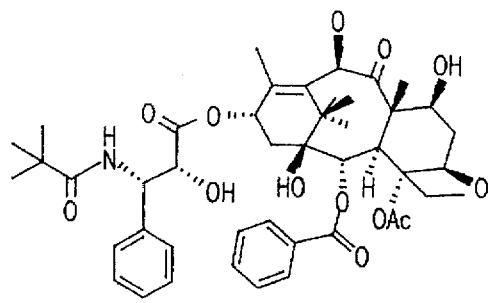
Figure 1:
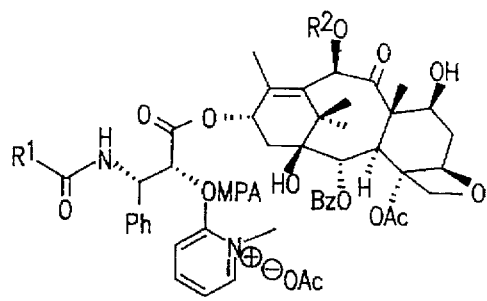
Figure 1:
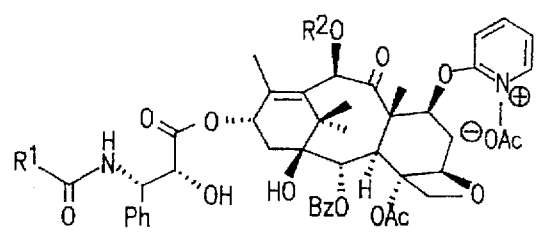
Figure 1:
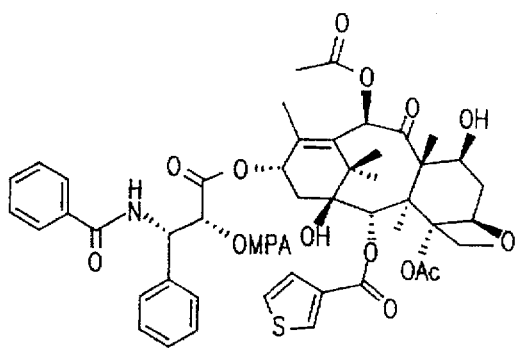
Figure 1:
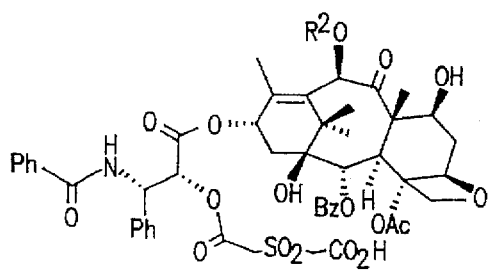

Athymic nude mice were purchased from Harlan-Sprague-Dawley. The animals were housed in microisolated cases under positive air pressure and all manipulations and drug treatments were performed in a laminar flow cabinet. Tumor cells were grown under the above tissue culture conditions. Cell suspensions in RPMI medium were injected S./C. Treatment was started one day after inoculation by i.p. injection of 400 μl drug solutions. Tumors were measured 3 times weekly in two dimensions, using calipers and tumor volume as calculated using the formula (V=w²×L×(3.142).

In Vivo Elimination

C-2'-MPA-Taxol (1 mM in 0.9% saline solution, 400 μL) was injected along with tritiated taxol at 32000 cpm into normal BALB/C mice (4 mice each) housed in metabolic cages and the urine and feces were measured periodically in a scintillation counter using Achillea scintillation fluid.

Cell Cultures

All cell lines described herein were obtained from the ATCC and maintained in media formulations as recommended by the supplier. The cell lines were tested for mycoplasma contamination prior to incubation at 37° C. in 5% carbon dioxide. Normal human dermal fibroblasts, peripheral blood lymphoblasts and mammary epithelial cells were obtained from Clonogenic Cor., San Diego, Calif. and were maintained under the above incubation conditions in special media provided by the supplier.

Cytotoxicity Assays

Antiproliferative activities of the onium salts were determined using the XTT dye binding assay. Cells were harvested with trypsin/EDTA (Irvine Scientific), washed, resuspended in the appropriate medium, and counted in a hemocytometer using Trypan Blue to determine viability. Then $10^4$ cells/well were added to 96 well microtiter plates and incubated for 24 hours before addition of drug at concentrations in the range of $10^{-4}$ to $10^{-13}$ molar by direct addition from DMSO solutions. After 72 hours, XTT binding dye was added and incubation was continued for 4 hours. The inhibition of cell proliferation was quantified using a Molecular Devices Microplate Reader. The absorbance of XTT was measured at 450 nM. The concentration of drug which inhibited growth of cells by 50% was calculated from duplicated determinations.

Plasma Stability and Prodrug Reversion

The stability of onium salts in human plasma at 37° C. was determined by ethyl acetate extraction of free compounds, followed by HPLC analysis of concentrates. Due to differences in the retention times under the HPLC conditions

TABLE I $IC_{50}$ Values [nM] For Paclitaxel Prodrugs Against A Panel Of Transformed And Untransformed Mammalian Cells

| Cell Line | Type | 1 | 2 | 3 | 4 | 5 | 6 |
|---|---|---|---|---|---|---|---|
| M-24 | Melanoma-metastatic | 0.018 | 0.35 | 0.62 | 0.54 | 0.017 | — |
| SK-Mel-28 | Melanoma | 524 | 87.9 | 702 | 110 | 614 | 68.2 |
| A-549 | Lung carcinoma | 5.79 | 152 | 42.5 | 2.35 | 0.80 | 0.72 |
| UCLA-P3 | Lung carcinoma | 0.66 | 2.44 | 12.8 | 1.88 | 0.12 | 19.9 |
| BT-549 | Breast carcinoma | 0.066 | 5.72 | 140 | 0.11 | 0.01 | 0.065 |
| U-2511 | CNS cancer | 15.6 | 860 | 170 | 31.7 | 21.0 | 0.61 |
| Capan 1 | Pancreas cancer | 0.967 | 5.70 | 34.5 | 0.35 | 0.011 | 0.59 |
| HT-29 | Colon carcinoma | 1.16 | 1.94 | 35.3 | 0.99 | 0.84 | 3.08 |
| OVCAR-3 | Ovarian carcinoma | 0.74 | 7.49 | 84.2 | 0.86 | 0.11 | 81.8 |
| SIHA | Squamous carcinoma | 8.89 | 3.78 | 8.79 | 7.55 | 1.56 | 4.12 |
| SK-N-SH | Neuroblastoma | 2.38 | 3.19 | 19.6 | 4.18 | 0.65 | 7.34 |
| 786-0 | Renal cell carcinoma | 10.8 | 27.4 | 454 | 11.5 | 41.5 | 0.56 |
| PC-3 | Prostate carcinoma | 1.01 | 6.47 | 70.7 | 1.15 | 0.46 | — |
| Molt-4 | T-cell leukemia | 0.096 | 7.07 | 9.94 | 0.066 | 0.01 | — |
| HL-60 | Promyelocytic | 0.061 | 0.25 | 5.85 | 0.12 | 0.035 | 0.89 |

TABLE I-continued $IC_{50}$ Values [nM] For Paclitaxel Prodrugs Against A Panel Of Transformed And Untransformed Mammalian Cells

| Cell Line | Type | 1 | 2 | 3 | 4 | 5 | 6 |
|---|---|---|---|---|---|---|---|
| L-1210 | leukemia Mouse leukemia | 3.24 | 12.8 | 178 | 1.20 | 0.59 | 0.019 |
| CHO | Chinese hamster ovary | 615 | 214 | 612 | 815 | 80 | 292 |
| HMEC | Mammary epithial cells | 62 | 127 | 81 | 219 | 32.9 | 56 |
| NHDF | Dermal fibroblast | 765 | 377 | 85.5 | 655 | 65 | 1.59 |
| RPMI-7666 | Blood lymphoblasts | 584 | 131 | 123 | 408 | 71.2 | 596 | used and differing ultraviolet absorption maxima between the prodrug and the drug, the stability was easily assayed using UV detection. In all the ensuing studies, the only degradation products detected were the taxoids and the pyridinone that results from the hydrolysis of the onium salts. In water, these compounds show surprising stability for up to weeks depending upon the storage conditions. The plasma half lives and fraction of free drug present are given in Table II. All three C-2' substituted MPA derivatives gave relatively short half lives of less than 14 minutes while the C-2' substituted acyl analog (7) had a half life of 100 minutes and the C-7 substituted derivative had a half life of 180 minutes. The fraction of ethyl acetated extractable material was between 18 and 23% for all onium salts and 95% for the present compounds. Since the partition coefficient for the organic-water phases for these compounds are greater than 50, the relatively low ethyl acetate extractable values given in Table II are most likely due to strong affinity of the onium salts for plasma proteins.

Cytotoxic Evaluations

Table I illustrates $IC_{50}$ values of six taxoids against a panel of human and murine tumor cell lines and, for comparison, against several untransformed cells. In general, the cytotoxic potencies of these analogs were comparable to their parent compounds within one to two logs of clear molar concentrations with medium values for tumor cell lines being in the nanomolar range. $IC_{50}$ values above the median were obtained for metastatic melanoma, melanoma, breast, ovarian, lung prostate and colon carcinomas, metastatic neuroblastoma and leukemia. Cell lines which gave relatively low cytotoxicities were melanoma, CNS cancer, and renal cell adenocarcinoma and untransformed cells. Taxotere (5) and its C-2' MPA salt (6)

TABLE II

SUMMARY OF PRECLINICAL RESULTS OF TAXOID DERIVATIVES

| | | Plasma Stability | | in vivo | | | |
|---|---|---|---|---|---|---|---|
| Compound | # | $t_{1/2}$ min | % EtAc extract-able | Tubulin Assay | anti-tumor effect | Animal Toxicity | % survival* |
| Taxol | 1 | stable | 95 | + | + | high | (0–20) |
| 2'-MPT-Taxol | 2 | 2.4 | 21 | − | + | low | (100) |

TABLE II-continued

SUMMARY OF PRECLINICAL RESULTS OF TAXOID DERIVATIVES

| Compound | # | Plasma Stability $t_{1/2}$ min | % EtAc extract-able | Tubulin Assay | in vivo anti-tumor effect | Animal Toxicity | % sur-vival* |
|---|---|---|---|---|---|---|---|
| 7-MPT-Taxol | 3 | 180 | 20 | + | – | low | (100) |
| 2'-MPT-3-Thiophene | 4 | 14 | 23 | – | – | low | (100) |
| 2'-Acyl-Taxol | 7 | 100 | 34 | – | – | low | (75) |
| Taxotere | 5 | stable | 95 | + | N.D. | N.D. | |
| 2'-MPT-Taxotere | 6 | 0.9 | 18 | – | N.D. | N.D. | |

*at end of experiments gave cytotoxicities about 10-fold higher than taxol or its opium salts, and the C-2'-MPA isomer of taxol (2) gave on average about 10-fold higher values than the C-7-isomer (3).

Effect of Taxol Derivatives on Microtubule Assembly-Disassembly

Figure 2:
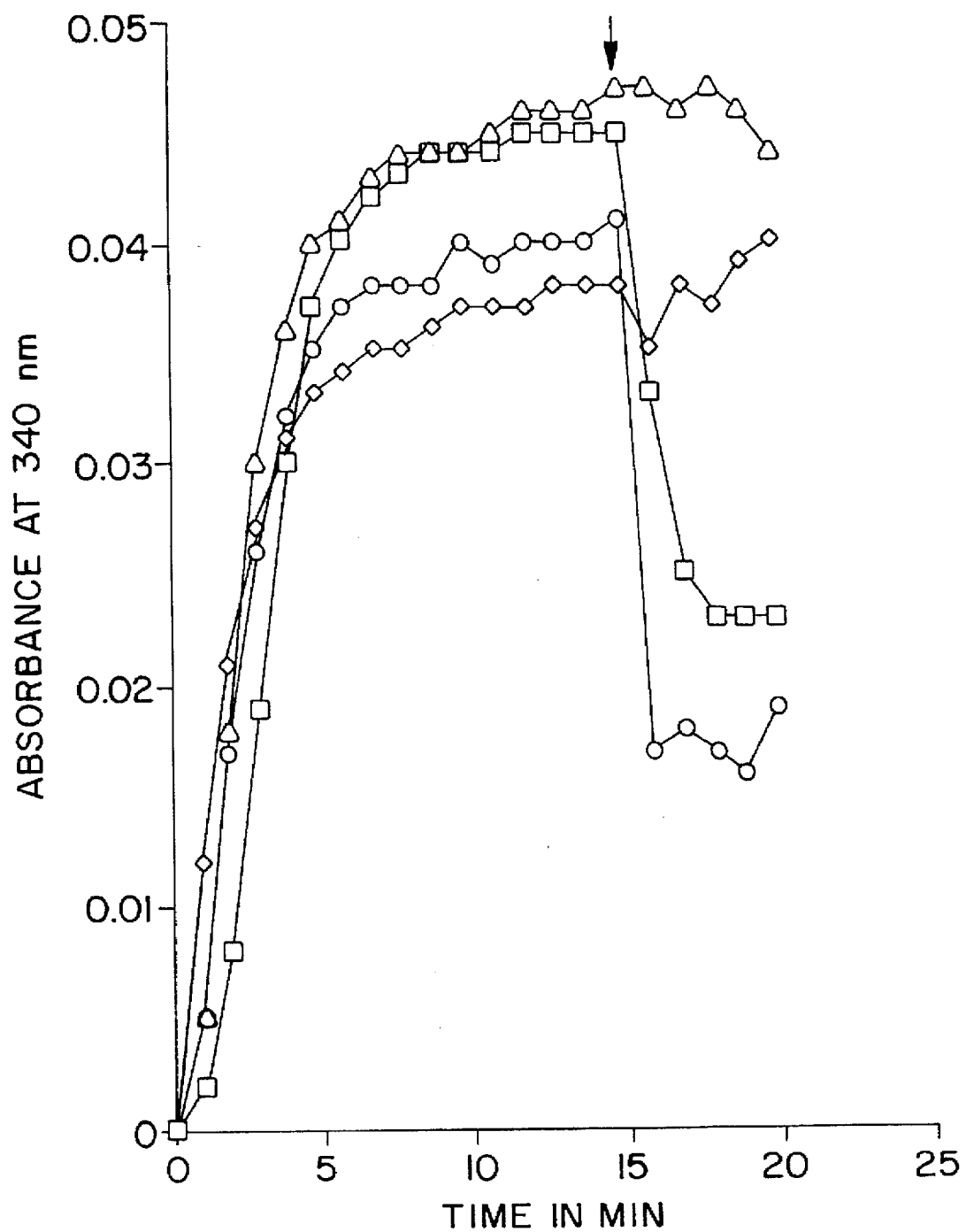
FIG. 2 illustrates tubulin polymerization-depolymerization measurements which disclose that calcium chloride promoted depolymerization is suppressed by taxol and taxol-7-MPA but not by taxol-2'-MPA. Data points for the negative control are indicated by (□); data points for the positive control using taxol are indicated by (◇); data points for taxol-7-MPA are indicated by (△); data points for taxol-2'-MPA are indicated by (○).

FIG. 2 illustrates the results of GTP induced polymerization and calcium chloride induced depolymerization of tubulin in the presence of taxol and the 2'- and 7-MPA substituted derivatives. The curves show that both taxol and its 7-MPA salt cause essentially complete inhibition of depolymerization of microtubules to tubulin, while the GTP controls and the 2' isomer showed the characteristic calcium induced depolymerization profiles, with about 70% reversal to tubulin. The C-2-substituted thiophene derivative inhibited depolymerization similar to taxol while compound (4), the 2'-MPA salt of this derivative, behaved in this assay similar to the C-2'-MPA isomer of taxol (2). These results confirm previous reports on the importance of the C-2' hydroxyl group for biological activity. HPLC analysis of the stability of these compounds also showed that both the 2'- and 7- isomers were completely stable under the assembly-disassembly conditions indicating that the 2'-isomers exhibit prodrug characteristics.

Specific Binding to Intact Cells

Figure 3:
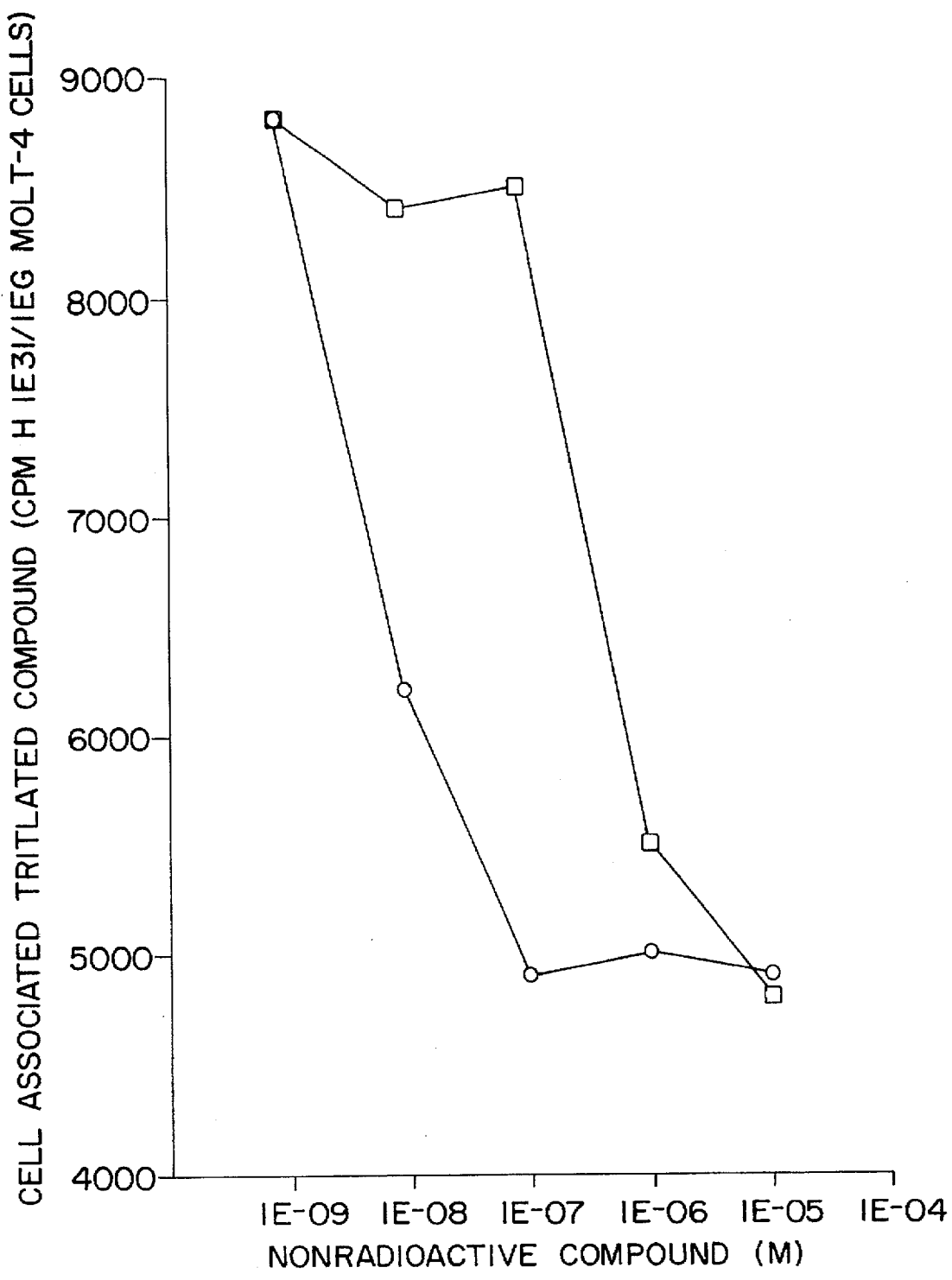
FIG. 3 illustrates the competition by nonradioactive taxol or c-2'-MPA-taxol for the binding of 1×10⁻⁹M tritiated compounds by intact Molt-4 cells.

FIG. 3 illustrates a competition assay of the C-2'-MPA isomer of taxol (2) in comparison to the parent taxol (1) for the suspension cell line Molt-4. The binding constants for taxols (1) and (2) calculated from the slopes of the linear portions of the curves in FIG. 3 were $5 \times 10^{-9}$ and $3 \times 10^{-6}$ respectively. It can be seen from these curves that binding is progressively inhibited at increasing concentrations of competitor until a plateau is reached. The plateau corresponds to nonspecific background binding. The curve obtained for the MPA-derivative parallels that for taxol but with an approximately 1000-fold lower specific binding affinity. The data agree with the results obtained from the microtubule assay suggesting that the cellular target for this drug is tubulin. Since the microtubule assay for compound (2) indicated no tubulin binding, the data in FIG. 3 suggests that the specific binding effect observed for this compound may involve a secondary target of lower affinity.

Antitumor Activity and Drug Elimination

Figure 5:
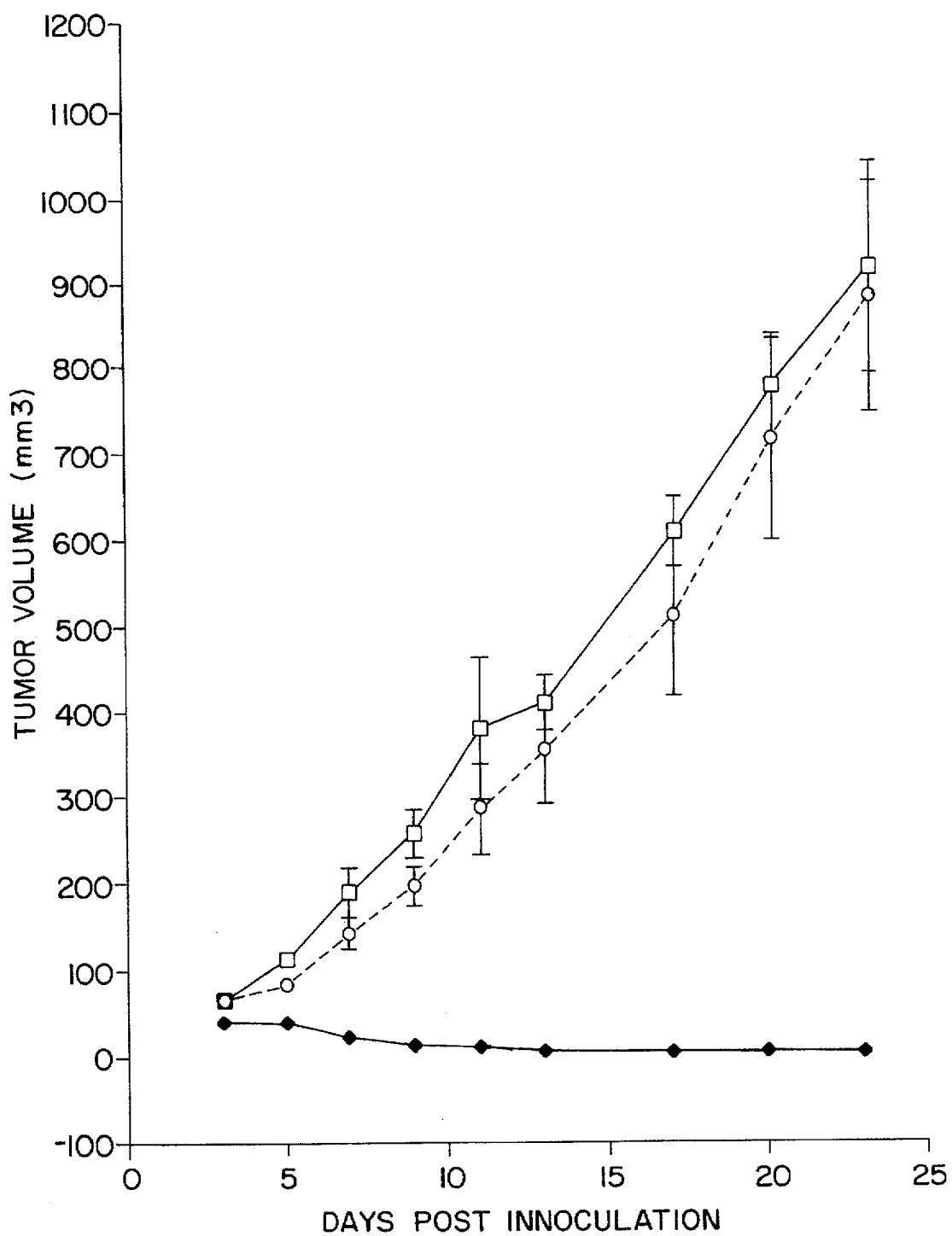
FIG. 5 illustrates the in vivo efficacy of protaxols in Ovcar 3 tumor xenograft nude mouse models. Data points for mice treated with D5W alone (control) are indicated by (□); data points for mice treated with 2' MPA-3-thiophene-taxol are indicated by (○); data points for mice treated with taxol-2'-MPA are indicated by (◇).
Figure 6:
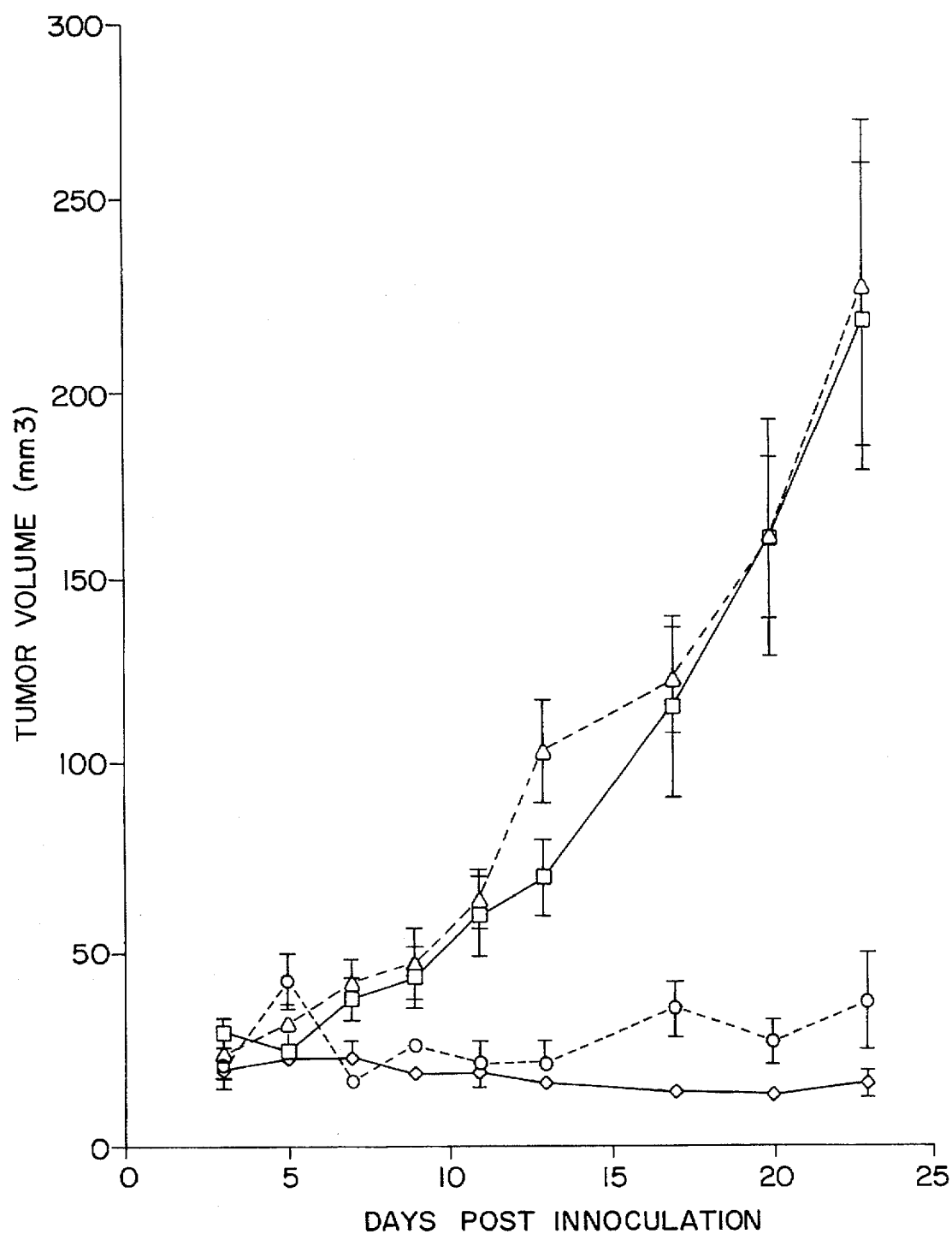
FIG. 6 illustrates the in vivo efficacy of protaxols in prostate tumor xenograft nude mouse models. Data points for mice treated with D5W alone (control) are indicated by (○); data points for mice treated with taxol-2'-MPA are indicated by (□); data points for mice treated with taxol are indicated by (△).

The antitumor activity of the onium salts of taxol were assessed in nude mice bearing tumors of human A-549 lung adenocarcinomas, Ovcar-3 ovarian carcinoma, and PC-3 prostate carcinoma cells. The data in FIG. 4 for the lung tumor model (A549) showed large differences in antiproliferation activity between two 2'-substituted protaxols. While the 2'-MPA derivative (2) inhibited tumor growth nearly completely, the 2'-acylsufone derivative (7) showed no significant growth inhibition, yielding a tumor growth curve very similar to the 5DW control. FIG. 5 illustrates antiproliferation results for 2'-MPA-3-thiophene-taxol (4) and 2' MPA taxol (2) for the Ovcar-3 human tumor xenograft. Under the conditions given in this figure, compound 2 gave complete inhibition of tumor growth, with 100% survival of animals. FIG. 6, summarizes the results for a PC-3, prostate tumor model study. Taxol was compared with both the 2'- and 7-substituted oxonium salts. The taxol (1) control and the 2'-MPA salt (2) gave regression of established tumors. The 7-MPA isomer (3) showed essentially no antitumor activity as indicated by a tumor growth curve which followed the 5DW controls. Most significantly, however, only 3 out of 8 mice survived the taxol treatment, while all of the mice given either the 2'- or 7-isomers survived and 5 out of 8 animals given the 2'-isomer showed complete remission with no palpable tumor mass at the termination of the trial (after 24 days). Tritiated taxol and 2' MPA-taxol were used in drug elimination experiments in normal BALB/C mice. In both groups of mice of four animals each, only 4–5% of the administered radioactivity was measured in the combined urine and feces 24 hours after injection.

Tubulin Polymerization-Depolymerization Measurements

Measurements comparing the relative suppression of calcium chloride promoted depolymerization of tubulin by taxol and taxol analogs are illustrated in FIG. 2. Tubulin was isolated from calf brain according to a procedure disclosed by Williams et al. (Methods in Enzymology, vol. 85, pages 376–392.) The tubulin was then stored at a concentration of 5.5 mg/ml in liquid nitrogen. 96-Well microplates were charged with 30 µl of PEM buffer and 10 ml DMSA containing the drug. Then 35 µl of tubulin solution (2 mg/ml) and 8 µl of GTP (1 mM) in water was added. The plates were then shaken on a titer plate shaker for 10 seconds and placed in the microplate reader. Absorbance was measured in 1 minute intervals at 340 nm at a plate temperature of 37° C. After 15 minutes of reaction time, 10 µl of calcium chloride (10 mM) was added and the reaction was continued for another 10 minutes.

Measurements were performed in 96 well plates at 37° C. following the protocol described by RB Weiss et al. (J. Clinical Oncology 1990: vol. 8, pages 1263–1268.) The addition of calcium chloride is illustrated in FIG. 2 by an arrow. In each case, 1.0 mM GTP was used to promote the initial polymerization of tubulin. Data points for the negative control are indicated by (□); data points for the positive control using taxol are indicated by (◊); data points for taxol-7-MPA are indicated by (Δ); data points for taxol-2'-MPA are indicated by (o). The negative control contained tubulin alone (1.0 mg/ml); CaCl$_2$ (0.25 mM) was added at 15 minutes. The positive control included both tubulin (1.0 mg·ml) with taxol ($10^{-6}$M), CaCl$_2$ (0.25 mM) added at 15 minutes. The taxol-2'-MPA measurements included both tubulin (1.0 mg·ml) with taxol-2'-MPA ($10^{-6}$M), CaCl$_2$ (0.25 mM) added at 15 minutes. The taxol-7-MPA measurement included both tubulin (1.0 mg·ml) with taxol-2'-MPA ($10^{-6}$M), CaCl$_2$ (0.25 mM) added at 15 minutes. Turbidity was measured as optical density at 340 nm using a microplate reader (Molecular Devices Thermomax).

Competition Measurements

The competition by nonradioactive taxol or c-2'-MPA-taxol for the binding of $1\times10^{-9}$M tritiated compounds by intact Molt-4 cells is illustrated in FIG. 3. Tritiated taxol (Moravek Corp.) was treated with 2-fluoropyridiunium tosylate according to the method of Nicolaou et al. to yield the C-2'-MPT-$^3$H-taxol. (Angew. Chem., Int. Ed. 1994: vol. 34, pp. 1583–1587.) Six well plates were incubated with $10^6$ Molt-4 cells in 50 mM phosphate buffered saline (PBS) or PRPMI media to which $10^{-9}$M of the radiolabeled taxol or taxol onium salt was added together with increasing concentrations of nonradiolabeled compound. After 30 minutes, the cells were centrifuged, washed with PBS and 1% SDS was added. The radioactivity of lysed cells was then read by means of a LKB Model 1219 scintillation counter. Alternatively, the cells may be lysed by sonication.

Synthesis of Taxoid-Onium Salts

Structures of compounds of this study are shown in FIG. 1. Taxol (1) was purchased from Napro Biotherapeutics Co. (Boulder Colo.). Taxotere (5) was synthesized from deacetyl-bacatin III according to conventional methods or obtained from Rhone Poulenc Rorer Research Development. C-7-MPA taxol (3) was synthesized according to the method of Paloma et al. (*Chemistry and Biology,* 1994: vol. 1, pp 107–1120.) The C-2'-methylpyridinium acetate salts (MPA) of taxol (2) and taxotere (6) and the 2-substituted thiophene analog (4) were synthesized according to the method of Nicolaou et al. (*Angew Chem., Int Ed.,* (1994): vol. 34, pp. 1583–15878; and *J. American Chemical Society* (1995): vol. 117, pp 2409–2420). Briefly, taxol (10.2 mg 0.012 mmol.) was dissolved in dichloromethane (0.4 mL) and treated sequentially at ambient temperature and under an atmosphere of dry argon with triethylamine (2 µl, 1.3 equiv.) and 2-fluoro-1-methylpyridinium tosylate (4.0 mg, 1.2 equiv.). The clear colorless solution rapidly turned to a clear pale yellow. The course of the reaction was monitored through thin layer chromatography (TLC) (E. Merck RP-18 silica, 65 tetrahydrofuran: 35 water, UV/phosphomolybdic acid) and after thirty minutes of stirring at ambient temperature, judged complete as no taxol remained and only one compound was apparent by TLC (Rf 0.8). Purification via reverse phase high pressure liquid chromatography (HPLC) ($C_{18}$ column, 1 mM $NH_4OAc$ pH 6.5 buffer/methanol gradient, 1.5 mL/min. UV) to give, after removal of solvent in vaccuo, pure taxol-2'-MPA (2) (12 mg, 93% yield) as a white amorphous solid.

Comparative Toxicities

Taxol (1) is formulated with Cremophor EL in order to enhance its solubility. Conventional formulations of taxol (1) with Cremophor EL exhibit a 50% lethality at 16–18 mg/kg in mice when given four times on alternating days, i.e., injections of 16–18 mg/kg of taxol (1) were administered on days 1, 3, 5, and 7. The dose of 16–18 mg/kg is approximately equivalent to 1,120–1,260 mg/m². Conventional formulations of taxotere (5) exhibit a 50% lethality and toxicities at generally lower dosages as compared to taxol. In contrast, Cremophor EL free formulations of the C-2'-MPA prodrugs of taxol (2) and taxotere (6) exhibit no lethality and minimal toxicity in mice at dosages of up to 70 mg/kg (approximately 4900 mg/m²) when administered four times on alternating days as above.

Formulations

Preferred therapeutic dose for the C-2'-MPA prodrugs of taxol (2) and taxotere (6) ranges between 5 and 70 mg/kg (approximately 1,120–1,260 mg/m²). However, for highly refractory tumors, the dose may be increased to 300 mg/kg (approximately 21,000 mg/m²) and in some cases to 400 mg/kg (approximately 28,000 mg/m²). The dose may be administered as a bolus injection or by i.v. infusion. Bolus injections may be administered intraveneously (i.v.) or intraperitoneally (i.p.). Bolus injections may be administered in a 10 ml volume. Alternatively, the dose may be administered by infusion in a much larger volume over a preferred period of three hours. The preferred interval between administrations is three weeks. However, for highly refractory tumors, the interval between administrations may be shortened.

There are two preferred formulations of the C-2'-M2PA prodrugs of taxol (2) and taxotere (6) for bolus injections:

1. 250 mg of C-2'-MPA prodrugs of taxol (2) or taxotere (6) is dissolved in 2–3 ml of ethanol, followed by dilution with 10–15 ml of 0.9% saline solution.

2. 250 mg of C-2'-MPA prodrugs of taxol (2) or taxotere (6) is dissolved in 2–3 ml of ethanol, followed by dilution with 10–14 ml of 5% dextrose solution or by 10–15 ml of 5% dextrose.

Formulations intended for infusion may contain other counter ions, e.g., lactated ringer solutions. Formulation may also include nitrates. The preferred counter ion is acetate. However, alterative counter ions include $OAc^-$, $Cl^-$, $Br^-$, $I^-$, $BF_4^-$, $ClO_4^-$, $ArSO_3^-$, and $AlkylSO_3^-$. More generally, any counter ion classified by the U.S. Food and Drug Administration as generally regarded as safe (GRAS) for injection may be employed in the formulation.

C-2'-MPA prodrugs of taxol (2) and taxotere (6) are stable and may stored without significant loss in 1–2% Tween #80 or Tween #20 (Sigma Chemical Co., St Louis Mo.) with or without ethyl alcohol.

EXAMPLE 1

Figure 4:
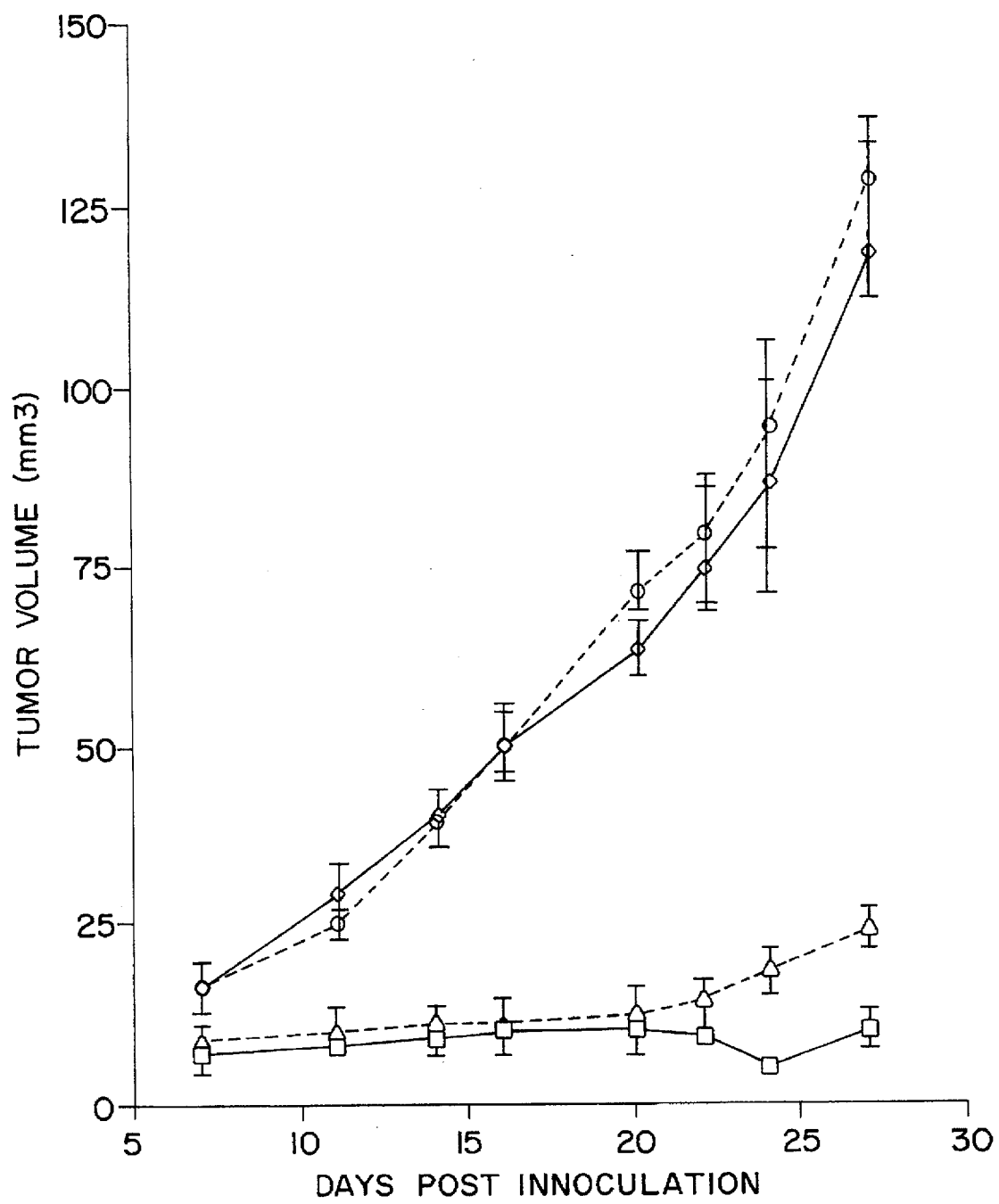
FIG. 4 illustrates the in vivo efficacy of protaxol in human lung adenocarcinoma tumor xenograft nude mouse models. Data points for mice treated with D5W (control) are indicated by (▲); data points for mice treated with 2'-acyl sulfone taxol are indicated by (□); data points for mice treated with taxol are indicated by (○); data points for mice treated with taxol-2'-MPA are indicated by (◇).

In Vivo Efficacy of Protaxols in Human Lung Adenocarcinoma Tumor Xenografts The in vivo efficacy of protaxols in human lung adenocarcinoma tumor xenograft nude mouse models is illustrated in FIG. 4. The tumor model was generated from A549 cell line, an ATTC that was maintained under standard cell proliferation conditions (37° C., 5% carbon dioxide in sterile air). Each cohort was comprised of six randomly chosen female athymic nude mice, for a total population size of twenty four mice. Hemocytometer counted cells, suspended in Hanks mediun (Gibco, Grand Island N.Y.) were implated S.C. ($10^6$ cells in 0.4 mL per mouse). Solid tumor growth was measured on each third day. Equimolar amounts of the test compounds (1.0 mM, 400 µL) were injected i.p. on days 1, 3, 5, 7, 9, and 11 using the following media:

(Δ): Control, saline in 5× distilled water (5 DW)

(o): Taxol (18.0 mg/kg of animal weight or approximately 1,260 mg/m²) suspended in Cremaphor/D5W (□) 2'-Acyl sulfone taxol dissolved in D5W (26.0 mg/kg of animal weight or approximately 1,820 mg/m²)

(◊)) Taxol-2'-MPA dissolved in D5W (23.9 mg/kg of animal weight or approximately 21,000 mg/m²).

EXAMPLE 2

In Vivo Efficacy of Protaxols in Ovcar 3 Tumor Xenografts

The in vivo efficacy of protaxols in Ovcar 3 tumor xenograft nude mouse models is illustrated in FIG. 5. The tumor model was generated from an ATTC Ovcar 3 carcinoma cell line that was maintained under standard cell proliferation conditions, viz. 37° C., 5% carbon dioxide in sterile air. Each cohort was comprised of eight randomly chosen female athymic nude mice, for a total population size of twenty four. Hemocytometer counted cells, suspended in Hanks medium (Gibco, Grand Island N.Y.) were implanted S.C. ($10^6$ cells in 0.4 mL per mouse). Solid tumor growth was measured on each third day. Equimolar amounts of the test compounds (1.0 mM, 400 µL) were injected i.p. on days 1, 3, 5, 7, 9, and 11 using the following media:

(□): Control, saline in 5× distilled water (D5W)

(○): 2" MPA-3-thiophene-taxol/D5W (◊) Taxol-2'-MPA dissolved in D5W (23.9 mg/kg of animal weight or approximately 1,673 mg/m$^2$).

EXAMPLE 3

In Vivo Efficacy of Protaxols in Prostate Tumor Xenografts

The in vivo efficacy of protaxols in prostate tumor xenograft nude mouse models is illustrated in FIG. 6. The tumor model was generated from an ATTC PC-3 prostate carcinoma cell line that was maintained under standard cell proliferation conditions, viz. 37° C., 5% carbon dioxide in sterile air. Each cohort was comprised of eight randomly chosen female athymic nude mice, for a total population size of twenty four. Hemocytometer counted cells, suspended in Hanks mediun (Gibco, Grand Island N.Y.) were implanted S.C. ($10^6$ cells in 0.4 mL per mouse). Solid tumor growth was measured on each third day. Equimolar amounts of the test compounds (1.0 mM, 400 µL) were injected i.p. on days 1, 3, 5, 7, 9, and 11 using the following media:

(○): Control, 5% dextrose in 5× distilled water (5 DW)

(Δ): Taxol (18.0 mg/kg of animal weight or approximately 1.260 mg/m$^2$) suspended in Cremaphor/D5W (□) Taxol-2'-MPA dissolved in D5W (23.9 mg/kg of animal weight or approximately 1,673 mg/m$^2$)

In each example, the procedures used for the maintenance of tumors and the experimental details conformed with protocols set forth by the Developmental Therapeutics Program, National Cancer Institute (NCI). Inferences about efficacy were drawn by ANOVA followed by protected t-test. For example: Day 9 (worst case) after application of ANOVA shows significant variance at the 0.06 level; the t-test shows that taxol and taxol-2'-MPA are significantly different from the control at the 0.04 level. After day 9, each data set is significantly different from the others at better than 0.05 confidence limit. Data shown as mean value with standard error.

What is claimed is:

1. A method for treating a mammal having a tumor or other cancer by administering an aqueous solution of a taxoid onium salt prodrug to the mammal by a route selected from the group consisting of injection and infusion, wherein the taxoid onium salt prodrug is represented by the following structure:

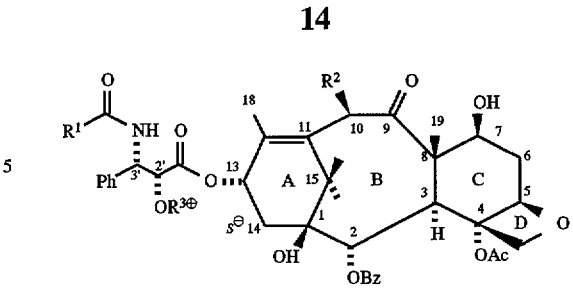

wherein S$^-$ is selected from the group consisting of OA$^-$, Cl$^-$, Br$^-$, I$^-$, BF$_4^-$, ClO$_4^-$, ArSO$_3^-$, and AlkylSO$_3^-$, R$^1$ is selected from the group consisting of phenyl and tBuO, R$^2$ is selected from the group consisting of OAc and OH, and R$^3$ is represented by the following structure:

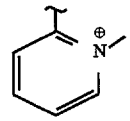

2. A method as described in claim 1 wherein the mammal is a human tumor or cancer patient.

3. A method as described in claim 1 wherein the mammal is sensitive and/or intolerant to a side effect of taxol.

4. A method as described in claim 1 wherein the method has a dosage range of approximately 50–300 mg/m$^2$.

5. A method as described in claim 1 wherein the method has a dosage range of approximately 50 and 4,900 mg/m$^2$.

6. A method as described in claim 1 wherein the method has a dosage range of approximately 50 and 21,000 mg/m$^2$.

7. A method as described in claim 1 wherein the method has a dosage range of approximately 50 and 28,000 mg/m$^2$.

8. A method as described in claim 7 wherein the tumor or other cancer is refractory and/or insensitive to taxol.

9. A method as described in claim 1 wherein S$^-$ is any counter ion classified as generally regarded as safe (GRAS) by the U.S. Food and Drug Administration.

10. A method as described in claim 1 wherein the taxoid onium salt prodrug is taxol-2'-MPA represented by the following structure:

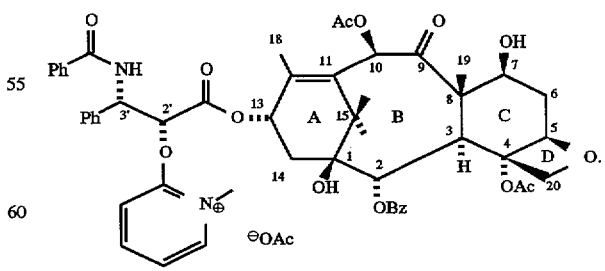

11. A method as described in claim 1 wherein the taxoid onium salt prodrug is taxotere-2'-MPA represented by the following structure:

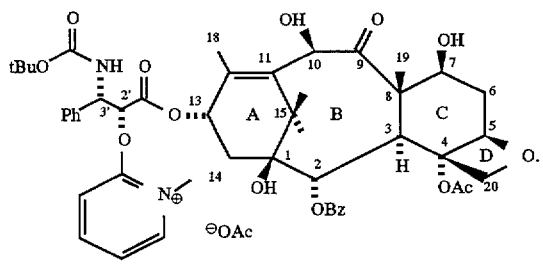

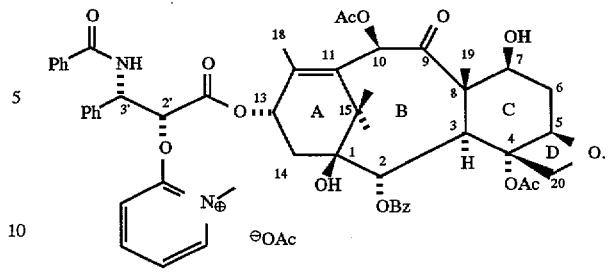

12. A method as described in claim 1 wherein the route of administration is by injection of a bolus.

13. A method as described in claim 1 wherein the route of administration is by infusion.

14. A method as described in claim 1 wherein the administration is intravenous.

15. A method as described in claim 1 wherein the administration is intraperitoneal.

16. A taxoid onium salt prodrug taxol-2'-MPA represented by the following structure:

17. A taxoid onium salt prodrug taxotere-2'-MPA represented by the following structure:

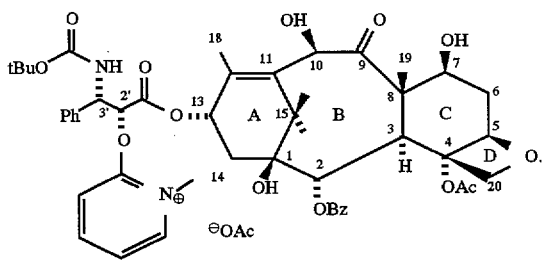

* * * * *